(12) United States Patent
Redkar et al.

(10) Patent No.: US 6,881,744 B2
(45) Date of Patent: Apr. 19, 2005

(54) CARBINOXAMINE TANNATE

(75) Inventors: Sham N. Redkar, Bound Brook, NJ (US); Dina Donatiello, Old Bridge, NJ (US); Timothy N. Truong, Lansdale, PA (US); Vilas M. Chopdekar, Edison, NJ (US)

(73) Assignee: Jame Fine Chemicals, Inc., Bound Brook, NJ (US)

( * ) Notice: Subject to any disclaimer, the term of this patent is extended or adjusted under 35 U.S.C. 154(b) by 39 days.

(21) Appl. No.: 10/326,349

(22) Filed: Dec. 20, 2002

(65) Prior Publication Data

US 2003/0114391 A1 Jun. 19, 2003

Related U.S. Application Data

(63) Continuation-in-part of application No. 10/017,131, filed on Dec. 14, 2001, now Pat. No. 6,677,381.

(51) Int. Cl.[7] .................. A61K 31/44; A61K 31/137; C07C 69/88; C07D 213/54; C07D 211/70
(52) U.S. Cl. ................... 514/357; 514/23; 514/649; 546/329; 546/333; 560/68
(58) Field of Search .................. 514/23, 357, 649; 560/68; 546/329, 333

(56) References Cited

U.S. PATENT DOCUMENTS

| | | | |
|---|---|---|---|
| 3,282,789 A | 11/1966 | Marty et al. | 167/82 |
| 5,599,846 A | 2/1997 | Chopdekar et al. | 514/653 |
| 5,663,415 A * | 9/1997 | Chopdekar et al. | 560/68 |
| 6,037,358 A | 3/2000 | Gordziel | 514/357 |
| 6,287,597 B1 * | 9/2001 | Gordziel | 424/464 |
| 6,306,904 B1 | 10/2001 | Gordziel | 514/530 |
| 6,509,492 B1 * | 1/2003 | Venkataraman | 560/68 |
| 2003/0050252 A1 | 3/2003 | Kiel et al. | 514/23 |
| 2003/0077321 A1 | 4/2003 | Kiel et al. | 424/465 |

FOREIGN PATENT DOCUMENTS

| | | | |
|---|---|---|---|
| JP | 54034814 | 4/1974 | |
| WO | WO 02/05745 A2 | 1/2002 | |
| WO | WO 02/05746 A3 | 1/2002 | ........... C07C/69/88 |
| WO | WO 02/05747 A2 | 1/2002 | |

* cited by examiner

*Primary Examiner*—Cecilia J. Tsang
*Assistant Examiner*—Taylor V. Oh
(74) *Attorney, Agent, or Firm*—Jack Matalon

(57) ABSTRACT

The invention pertains to carbinoxamine tannate and to a method for preparing carbinoxamine tannate by reacting carbinoxamine free base at a temperature of about 50 to about 150° C. with tannic acid neat or as an aqueous slurry containing about 5 to about 30 wt. % water.

16 Claims, No Drawings

CARBINOXAMINE TANNATE

CROSS-REFERENCE TO RELATED APPLICATION

This application is a continuation-in-part of pending U.S. patent application Ser. No. 10/017,131 filed Dec. 14, 2001 now U.S. Pat No. 6,677,381.

FIELD OF THE INVENTION

The invention pertains to carbinoxamine tannate, its method of preparation and to pharmaceutical compositions containing carbinoxamine tannate.

BACKGROUND OF THE INVENTION

Carbinoxamine, i.e., 2-[(4-chlorophenyl)-2-pyridinylmethoxy]-N,N-dimethyl-ethanamine, is a well-known antihistamine. The compound has the molecular formula $C_{16}H_{19}ClN_2O$, a molecular weight of 290.79 and is a liquid having a boiling point (0.1 mm Hg) of 158–162° C. The 1-form has a boiling point (0.5 mm Hg) of 143–144° C., a density (at 20° C.) of 1.5522 and an optical rotation of $[\alpha]_D^{25}$ –6.8° (c=2 in methanol, while the d-tartrate salt of the 1-form has a melting point of 143–144.5° C. and an optical rotation of $[\alpha]_D^{25}$ +37.2°(c=20 in methanol. Since carbinoxamine is insoluble in water, it typically is administered in the form of the hydrochloride, maleate or tartrate salt which is freely soluble in water. It is most often administered in the form of its maleate salt which has a melting point of 117–119° C. It is typically administered to human beings in need of such medication in the form of a syrup, tablet and/or suspension. It frequently is administered in combination with one or more other antihistamine and/or antitussive compositions, e.g., diphenhydramine hydrochloride, chlorpheniramine maleate, dextromethorphan hydrobromide monohydrate, etc.

The currently administered forms of carbinoxamine, i.e., generally an acid salt such as the hydrochloride, maleate or tartrate are disadvantageous in that they are absorbed very quickly in the mammalian body. Accordingly, although such forms provide prompt relief, multiple doses must be taken on a daily basis to provide an effective level of medicament over the prescribed period of treatment (generally several days to one week). It would be very desirable if a form of was available that would have extended-release properties, i.e., the carbinoxamine would be slowly released into the patient's bloodstream over a prolonged period of time. Until recently, the only slow-release forms of carbinoxamine that were available were those such as polymer-coated tablets. Such prior art formulations provided mixed results in that the carbinoxamine was not available for adsorption into the patient's bloodstream until the polymeric coating was dissolved, but thereafter the carbinoxamine was quickly absorbed and metabolized. The result is that frequently, the carbinoxamine had to again be administered to the patient within the period of only a few hours.

The foregoing problem was solved by converting the carbinoxamine free base into its tannate salt by reaction of the free base with tannic acid. The tannate salt stabilizes the carbinoxamine free base and most importantly, imparts extended release properties to the carbinoxamine. In recent years, tannate salts of antihistamines have become known, e.g., see U.S. Pat. Nos. 5,599,846; 5,663,415; 6,037,358, 6,287,597, and 6,306,904.

Tannic acid is commercially available and is used in many industrial applications. It is frequently referred to as gallotannic acid, gallotanin; glycerite or tannin. It is a pale tan powder having a decomposition point of 210–215° C., and is highly soluble in water and alcohols. Its molecular formula is $C_{76}H_{52}O_{46}$ and its CAS number is 1401-55-4. Tannic acid is typically produced from Turkish or Chinese nutgall and has a complex non-uniform chemistry and typically contains about 5–10 wt. % water.

Commercially available antihistamine tannate compositions are relatively impure. Such compositions are typically prepared by reacting the antihistamine free base with tannic acid in the presence of a volatile solvent, usually isopropanol. The yield is only fair (e.g. about 70%) and decomposition products e.g. 2–5 wt. %, and a significant amount of the volatile solvent, e.g. 6–10 wt. %, based on the weight of the composition, remains with the product and cannot be removed.

Typically, in the conventional isopropanol route, the antihistamine free base and the tannic acid will be present in the isopropanol at a concentration of about 20wt. %, based on the weight of the reaction mixture. The reaction mixture is stirred for about one hour, while maintaining a temperature of 60–70° C. The reaction mixture is cooled to room temperature and filtered. The precipitate is vacuum dried for an extended period of time at a temperature of 60–80° C. A yield of product of only about 70% is obtained and the product purity will be about 85–90 wt. %, based on the weight of the composition (the impurities consist of isopropanol and decomposition products which cannot be removed).

Many antihistamine tannates are heat sensitive and therefore undergo decomposition quite readily upon prolonged exposures to temperatures as low as 50° C. Accordingly, even when the solvent utilized in its preparation has a relatively high vapor pressure such as is in the case of isopropanol, it is impossible to reduce the solvent content below about 6 wt. %, based on the weight of the antihistamine tannate composition, even at reduced pressures and very mild elevated temperatures. Moreover, from an environmental point, it would be most desirable if the antihistamine tannate could be prepared such that the use of volatile solvents could be avoided.

The process disclosed in U.S. Pat. No. 5,663,415 represents a significant improvement over the isopropanol route. The process disclosed in the '415 patent involves three steps:

(a) the antihistamine in the form of its free base is contacted with tannic acid in the presence of water at a maximum temperature which will not cause decomposition of the antihistamine tannate to an extent of greater than about 5 wt %, based on the weight of the antihistamine tannate, (b) the antihistamine is allowed to remain in contact with the tannic acid in the presence of water for a period of time of about 5 minutes to 4 hours at said maximum temperature; and (c) the antihistamine tannate resulting from step (b) is freeze-dried at a temperature and at a reduced pressure and for such period of time that (i) at least about 90 wt. % of the water is removed from the antihistamine tannate and (ii) decomposition of the antihistamine tannate will be limited to a maximum of about 5 wt. %.

The '415 patent discloses a three-step method that results in the production of pure antihistamine tannate compositions having a minimum purity level of at least 90 wt. %, usually at least 95 wt. % and often at least 98 wt. %, based on the weight of the composition, with a yield of at least about 90% and often with a yield in excess of 97%. The chief "impurity" present in the compositions prepared by the process of the '415 patent is water which is present in an amount of 1–5 wt. %, based on the weight of the composition. However, the '415 patent does not disclose carbinoxamine tannate.

Although the process disclosed in the '415 patent represents a dramatic improvement leading to very pure antihistamine tannate compositions, it has several drawbacks: freeze-drying is quite time-consuming (typically 30–36hours to remove 1 liter of water) and expensive and requires specialized equipment in order to achieve the reduced pressures and temperature required to dry the antihistamine tannate composition, i.e., a pressure of not greater than about 500 milliTorr and a temperature in the range of about −60° C. to −20° C. Such specialized equipment also limits the amount of product that can be processed within a reasonable amount of time.

It has now been found that by the process of this invention, it is possible, to convert carbinoxamine into carbinoxamine tannate and unexpectedly, the carbinoxamine does not undergo racemization in the course of its conversion to the tannate. This was quite surprising since a similarly useful antihistamine, e.g., levo-phenylephrine, undergoes racemization when it is reacted with tannic acid by the hot melt process of the invention to produce the tannate salt.

DETAILED DESCRIPTION OF THE INVENTION

In accordance with the process of the invention, carbinoxamine tannate is prepared by reacting carbinoxamine free base with tannic acid. If the carbinoxamine is present in the form of a salt (typically a maleate), the salt is neutralized with a stoichiometric amount of a base such as aqueous sodium or potassium hydroxide (e.g., 10 wt % concentration) and the resulting carbinoxamine layer is washed free of salts. The carbinoxamine free base is heated to a temperature of about 50 to about 150° C., preferably 70 to 120° C., and tannic acid is slowly added, while mixing, to the carbinoxamine free base over a period of a few minutes to about one hour. The reaction mixture is continuously stirred while maintaining such temperature range for a period of about 10 minutes to about 2 hours. Thereafter, the reaction mixture is cooled to room temperature. If the process is carried out with the tannic acid utilized neat, the resultant product need not be dried (it will, however, contain 1–3 weight percent of water since the tannic acid as commercially available contains 5–10 wt. % water). After any desired drying, the product is preferably milled to form a free-flowing powder preferably to a particle size of about 50 to about 200 mesh.

As mentioned above, the tannic acid may be utilized neat, i.e., no additional diluent or solvent is employed during the reaction. However, the reaction mixture without any added water is very viscous. Therefore, water, e.g. 5–30 wt. %, may be added to facilitate the stirring of the reaction mass. If desired, any such added water may ultimately be removed from the reaction product in a separate step by well-known processes, e.g. drying under vacuum (about 1 mm Hg) at about 65 to about 75° C. for 1–10 hours or more, sparging with nitrogen for 1 to 10 hours or more, etc.

The molar ratio of the carbinoxamine free base to the tannic acid is generally in the range of about 4 to about 8, preferably 5 to 6, moles of carbinoxamine free base per mole of tannic acid.

The carbinoxamine tannate prepared by the process of the invention will have a softening point which is inversely related to the moisture content (as determined by Karl Fischer analysis) as may be seen from the following table:

| Softening Point, °C. | Moisture Content, % (K.F.) |
|---|---|
| 58–63 | 8.7 |
| 69–74 | 5.5 |
| 78–83 | 2.6 |
| 125–130 | 0.9 |

The carbinoxamine tannate prepared by the process of the invention may be prepared for administration in the form of pharmaceutically acceptable compositions such as powders, capsules, elixirs, syrups, nasal sprays, etc.

Tablets containing the carbinoxamine tannate may be prepared in a conventional manner by the addition of suitable pharmaceutical carriers, including fillers, diluents, lubricants and the like as well as conventional and well known binding and disintegrating agents. Atypical tablet composition of the present invention will contain, in addition to the phenylephrine tannate, microcrystalline cellulose, corn starch, magnesium stearate, croscarmellose sodium and coloring matter.

The suspension formulations of the carbinoxamine tannate will typically additionally contain citric acid, caramel, glycerin, sorbitol solution, propylene glycol, saccharin sodium, sodium benzoate, flavoring agent and purified water.

If desired, the carbinoxamine tannate prepared by the process of the invention may be formulated with other pharmaceutically active ingredients such as expectorants, antihistamines and antitussives, e.g., dextromethorphan, chlorpheniramine, dextrochlorpheniramine, brompheniramine, dextrobrompheniramine, pyrilamine, phenylephrine, ephedrine, carbetapentane, guaifenesin, and the like. Typically, these other active ingredients may be employed in the form of their free bases or as their salts, e.g., citrates, maleates, hydrobromides, hydrochlorides, tannates, etc.

The following nonlimiting examples shall serve to illustrate the present invention. Unless otherwise indicated, all parts and percentages are on a weight basis.

EXAMPLE 1

Carbinoxamine free base was prepared from commercially available carbinoxamine maleate as follows.

Carbinoxamine maleate in the amount of 300 g (1.03 moles) was placed in a 2 liter flask and thereafter 640 g of a 10% aqueous solution of sodium hydroxide were charged to the flask with stirring. The reaction mixture was heated to a temperature of 45–55° C. with stirring for about 30 minutes. Thereafter, stirring was discontinued and the reaction mixture was allowed to settle. The upper organic layer was separated and mixed, with stirring, with 300 g of water and heated to a temperature of 70–75° C. for several minutes. The mixture was then allowed to settle and the lower organic layer was recovered. The yield of the carbinoxamine free base was 225 g (96.5% of theory on an anhydrous basis).

EXAMPLE 2

Carbinoxamine tannate was prepared from the carbinoxamine free base prepared in Example 1 and tannic acid as follows.

Water in the amount of 12 g was charged to a 500 ml beaker and heated to 75–85° C. 78.4 g of carbinoxamine free base (K.F. moisture content of 7.8%) was added with stirring while maintaining the temperature of 75–85° C. Thereafter, 89.1 g of tannic acid (K.F. moisture content of 4.8%) were charged to the beaker over a period of about 30 minutes, with stirring, while maintaining a temperature of 75–85° C. A uniformly viscous slurry resulted and this slurry was then poured into a glass dish and allowed to cool to room temperature. The reaction product was then pulverized and the powder was determined to have a K.F. moisture content of 8.7% and a softening point of 58–63° C.

A portion of the reaction product was dried in a vacuum oven and dried at 50° C. to a K.F. moisture content of 2.6%; the dried product had a softening point of 78–83° C. The base assay was 44.2% as is (45.4% on an anhydrous basis). The reaction product was subjected to HPLC analysis which indicated no significant level of impurity.

The reaction product was vacuum dried to a K.F. moisture content of 0.9%; such dried product had a softening point of 125–130° C. A 2 g aliquot sample of such dried product was mixed with 110 g of methylene dichloride, stirred for 10 minutes and then filtered. The filtrate was evaporated to dryness and 0.0178 g of methylene dichloride-soluble material was obtained. The weight of the methylene dichloride-insoluble carbinoxamine tannate product was 2.0061 g. Based on the following equation, a reaction completion of 99.11% was obtained: 100−100 (0.0178/2.0061)=99.11%

What is claimed is:

1. A method for preparing carbinoxamine tannate comprising reacting carbinoxamine free base with tannic acid neat at a temperature of about 50 to 150° C. and thereafter recovering the resultant carbinoxamine tannate.

2. The method of claim 1 wherein the reaction is carried out at a temperature of 70 to 120° C.

3. The method of claim 1 wherein the carbinoxamine free base is employed in an amount of about 4 to about 8 moles of the free base per mole of tannic acid.

4. The method of claim 3 wherein the carbinoxamine free base is employed in an amount of 5 to 6 moles of the free base per mole of tannic acid.

5. The method of claim 1 wherein the recovered carbinoxamine tannate is subsequently dried under vacuum at a temperature of about 50 to about 75° C. for a period of 1 to 10 hours or more.

6. The method of claim 1 wherein the recovered carbinoxamine tannate is dried by sparging with nitrogen for a period of 1 to 10 hours or more.

7. The method of claim 1 wherein the recovered carbinoxamine tannate is milled to provide a free-flowing powder.

8. The method of claim 7 wherein the powder has a particle size in the range of about 50 to about 200 mesh.

9. A method for preparing carbinoxamine tannate comprising reacting carbinoxamine free base with tannic acid in the presence of about 5 to about 30 wt. % water at a temperature of about 50 to 150° C. and thereafter recovering the resultant carbinoxamine tannate.

10. The method of claim 9 wherein the reaction is carried out at a temperature of 70 to 120° C.

11. The method of claim 9 wherein the carbinoxamine free base is employed in an amount of about 4 to about 8 moles of the free base per mole of tannic acid.

12. The method of claim 9 wherein the carbinoxamine free base is employed in an amount of 5 to 6 moles of the free base per mole of tannic acid.

13. The method of claim 9 wherein the recovered carbinoxamine tannate is subsequently dried under vacuum at a temperature of about 50 to about 75° C. for a period of 1 to 10 hours or more.

14. The method of claim 9 wherein the recovered carbinoxamine tannate is dried by sparging with nitrogen for a period of 1 to 10 hours or more.

15. The method of claim 1 wherein the recovered carbinoxamine tannate is milled to provide a free-flowing powder.

16. The method of claim 15 wherein the powder has a particle size in the range of about 50 to about 200 mesh.

* * * * *